US009330578B2

(12) United States Patent
Tian et al.

(10) Patent No.: US 9,330,578 B2
(45) Date of Patent: May 3, 2016

(54) INTELLIGENT TISSUE MIMICKING ULTRASONIC PHANTOM AND METHOD OF PREPARING THE SAME

(71) Applicant: Chongqing Haifu Medical Technology Co., Ltd., Chongqing (CN)

(72) Inventors: Yunbo Tian, Chongqing (CN); Fangwei Ye, Chongqing (CN)

(73) Assignee: Chongqing Haifu Medical Technology Co., Ltd. (CN)

( * ) Notice: Subject to any disclaimer, the term of this patent is extended or adjusted under 35 U.S.C. 154(b) by 0 days.

(21) Appl. No.: 14/684,745

(22) Filed: Apr. 13, 2015

(65) Prior Publication Data

US 2015/0213732 A1 Jul. 30, 2015

Related U.S. Application Data

(63) Continuation of application No. 12/918,625, filed as application No. PCT/CN2009/000161 on Feb. 17, 2009, now abandoned.

(30) Foreign Application Priority Data

Feb. 21, 2008 (CN) .......................... 2008 1 0007970

(51) Int. Cl.

| | |
|---|---|
| ***C08F 20/56*** | (2006.01) |
| ***C08F 22/36*** | (2006.01) |
| ***G09B 23/28*** | (2006.01) |
| ***A61B 17/00*** | (2006.01) |
| ***C08F 220/56*** | (2006.01) |
| ***C08L 33/26*** | (2006.01) |
| ***G01D 18/00*** | (2006.01) |
| *A61N 7/02* | (2006.01) |

(52) U.S. Cl.

CPC .............. *G09B 23/286* (2013.01); *A61B 17/00* (2013.01); *C08F 220/56* (2013.01); *C08L 33/26* (2013.01); *G01D 18/00* (2013.01); *A61B 2017/00707* (2013.01); *A61B 2017/00716* (2013.01); *A61N 7/02* (2013.01)

(58) Field of Classification Search

CPC ........... A61B 2017/00707; A61B 2017/00716; A61B 17/00; G09B 23/286; G01D 18/00; A61N 7/02; C08F 220/56; C08F 222/385; C08L 33/26

See application file for complete search history.

(56) References Cited

U.S. PATENT DOCUMENTS

| | | | |
|---|---|---|---|
| 5,672,656 | A | 9/1997 | Murayama et al. |
| 6,352,860 | B1 | 3/2002 | Madsen et al. |
| 6,960,617 | B2 | 11/2005 | Omidian et al. |

FOREIGN PATENT DOCUMENTS

| | | | |
|---|---|---|---|
| CN | 1328067 | A | 12/2001 |
| CN | 101293939 | | 10/2008 |
| JP | 6-116169 | A | 4/1994 |
| WO | 2009103220 | A1 | 8/2009 |

OTHER PUBLICATIONS

Journal of Chemistry; Thanh et al, vol. 44(1), pp. 100-104, 2006.*
Journal of Chemistry: Thanh et al.: vol. 44(1), p. 100-104; 2006.
Journal of Controlled Release: Dong et al.; 4 (1986), pp. 223-227.
English Translation of Wu et al.: Pharmaceutical Journal of Chinese People's Liberation Army vol. 23(4), 2007, 246-249.
Wu et al.: "Synthesis and Properties of Temperature-Sensitive Poly (N-isopropylacrylamine/acrylamide) nanogel" Pham J. Chin PLA, Aug. 2007, vol. 23, No. 4, pp. 245-249, ISSN 1008-9926.
Li et al.: "A Transparent Tissue-Mimicking Phantom for Evaluating the Focusing Performance of HIFU" Chinese Journal of Medical Imaging Technolgoy, 2006, vol. 22, No. 8, pp. 1261-1265.
First Office Action received in corresponding German Application (7 pages) Dated: Oct. 26, 2015.
Zhang, et al: Gaodeng Xuexiao Huaxue Xuebao (Chemical Journal of Chinese Universities), 2000, 21(8), S. 1309-1311 (with English language abstract).
Bao et al: Gongneng Gaofenzi Xuebao (Journal of Functional Polymers), 2004, 17(3), S. 447-451 (with English language abstract).

* cited by examiner

*Primary Examiner* — Karuna P Reddy
(74) *Attorney, Agent, or Firm* — Andrew J. Anderson, Esq.; Harter Secrest & Emery LLP

(57) ABSTRACT

An intelligent tissue mimicking ultrasonic phantom, which is a temperature-sensitive polymer gel having the following characteristics: acoustic velocity: 1500-1550 m/s; acoustic impedance: $(1.50\text{-}1.60)\times10^6$ Pa·s/m; density: 1.01-1.06 g/cm$^3$; and a denaturation temperature around which there is a reversible phase transformation between the opaque phase and the transparent phase. Said gel can be a polymer of isopropylacrylamide (NIPA). Said ultrasonic phantom has a transparent appearance, and an adjustable thermal denaturation temperature; the thermal denaturation region of the ultrasonic phantom is distinct and has a well-defined boundary; the material of the phantom is stable and deterioration-resistant, and can ensure the consistency of the quality; the phantom is thermal denaturable with the appearance thereof turning white, while the phantom recovers when the heat is removed, such that it can be used repeatedly.

20 Claims, No Drawings

INTELLIGENT TISSUE MIMICKING ULTRASONIC PHANTOM AND METHOD OF PREPARING THE SAME

FIELD OF THE INVENTION

The present invention relates to a biological tissue model. Specifically, the present invention relates to an intelligent tissue mimicking ultrasonic phantom and a method of preparing the same.

BACKGROUND OF THE INVENTION

Phantom is the abbreviation of biological tissue mimicking model. Currently, there are various ultrasonic phantoms, most of which are for applications of ultrasonic diagnosis, and for microwave hyperthermia and HIFU (High Intensity Focused Ultrasound) studies. However, the purpose of a phantom for ultrasound therapy is completely different from that of a phantom for ultrasound diagnosis. HIFU is applied in the treatment of tumor by causing coagulate tissue necrosis. Ultrasonic phantom for diagnosis is typically opaque, and cannot generate a macroscopic coagulation necrosis after HIFU radiation, although it has acoustic properties similar to those of a soft tissue.

HIFU is a newly immerging technology for treating tumor by a non-invasive, conformal thermal ablation method guided by ultrasound or MRI (Magnetic Resonance Imaging). During clinical treatment using a HIFU system, the HIFU system must be quality tested, i.e., effectiveness, safety, and reliability, wherein the most crucial test is the evaluation of the focusing performance of the HIFU treating applicator. The focusing performance of the HIFU treating applicator on the tissues is directly related to effectiveness, safety, and reliability of HIFU during clinical application. However, it is thus far difficult to evaluate the focusing performance of the HIFU treating applicator with a non-standardized biological tissue, and compare focusing performances of different HIFU treating applicators. Therefore, it is very important to establish a standardized, reusable transparent tissue mimicking phantom.

At present, the phantoms used in HIFU studies both in China and abroad are transparent tissue mimicking phantoms formed by a mixture mainly comprising polyacrylamide and protein (bovine serum or fresh egg white) that serves as a temperature-sensitive indicator. Upon HIFU radiation, protein undergoes thermal denaturation, and the appearance of the phantom turns cloudy or white, thereby revealing the focal region of the focused ultrasound (See Fa-qi LI, Ping M A, Xiao-qin K O U, et al, A transparent tissue-mimicking phantom for evaluating the focusing performance of HIFU, Chinese Journal of Medical Imaging Technology, 2006, 22(8): 1261-1265). However, this protein phantom has many disadvantages:

(1) The cloudy region is not stable, the boundary is not well-defined, and the properties are much inferior to those of BFR (Biological focal region, i.e., the coagulation necrosis region visible by naked eyes and confirmed by a microscope, which appears at the location of the acoustic focus in the biological tissue where HIFU radiation is applied. Reference: Yong-chang ZHOU, Wan-xue GUO. Ultrasound Medicine [M]. Fourth Edition. Beijing: Science Press, 2002.1780.) produced in biological tissues, therefore, this protein phantom is not very suitable for studying the focusing performance of HIFU in biological tissues.

(2) If bubbles are contained therein, the white region will become irregular.

(3) As a temperature-sensitive indicator, once protein is denatured by heat, its appearance then turns white and cannot be restored. Therefore, it can only be used once associated with high cost.

(4) Although additives such as preservatives and foam inhibitors can be incorporated therein, the main material (i.e., protein) is prone to deterioration, and therefore, the stability of the phantom and the effectiveness to eliminate the impact of bubbles in the preparation process are limited.

(5) As the source of transparent protein, bovine serum or fresh egg white cannot assure the consistency of its quality, therefore the consistency of the phantom also cannot be assured, and standardization of the phantom cannot be realized.

(6) Restricted by factors such as the nature of protein, visible change in the appearance can only be seen at a temperature of 70° C. or higher (i.e., the denaturation temperature of protein), and this temperature is higher than that at which coagulation necrosis occurs in real biological body tissues (typically 60-65° C.), and different biological body tissues may have different temperatures at which coagulation necrosis occurs. The denaturation temperature of the protein phantom is thus fixed, and the requirements of different denaturation temperatures cannot be satisfied. Therefore, a phantom that has a denaturation temperature below 70° C. and can be used at different denaturation temperatures are desired by those skilled in the art (See: Sam Howard, Jonathan Yuen, Paul Wegner, et al. Characterization and FEA Simulation for a HIFU Phantom Material. 2003 IEEE International Ultrasonics Symposium, 2003, Vol. 2: 1270-1272).

SUMMARY OF THE INVENTION

The technical problem to be solved by the present invention is directed to the above problems in the prior art. This invention provides an intelligent tissue mimicking ultrasonic phantom and a method of preparing the same, wherein the thermal denaturation temperature of the ultrasonic phantom is adjustable; the thermal denaturation region of the ultrasonic phantom is visibly distinct and has a well-defined boundary; the material of the phantom is stable and resists deterioration, and can ensure the consistency of the quality; the phantom is denatured by heat with the appearance thereof turning white, while the phantom recovers when the heat is removed, such that it can be used repeatedly.

To achieve the above objects, the present invention provides an intelligent tissue mimicking ultrasonic phantom which is a temperature-sensitive polymer gel having the following acoustic property and other physical characteristics (which are substantially the same as those of a biological tissue).

acoustic velocity: 1500-1550 m/s; acoustic impedance: $(1.50\text{-}1.60)\times10^6$ Pa·s/m; density: 1.01-1.06 g/cm$^3$; and a denaturation temperature, namely, a Lower Critical Solution Temperature (LCST) or a Volume Phase Transition Temperature at which the volume of the phantom changes, that is adjustable in the range of 30-70° C. by changing the ratio of raw materials, around which there is a reversible phase transformation between the opaque phase and the transparent phase in the gel. When radiated by focused ultrasound, the tissue mimicking ultrasonic phantom in the focal region of the focused ultrasound changes from a colorless and transparent appearance to a opaque white appearance when the temperature of the focal region reaches the denaturation temperature due to an accumulation of ultrasonic energy, such that the morphology of the focal region of the focused ultrasound is clearly shown. And when the irradiation with focused ultrasound is stopped, the temperature of the focal region turns below the denaturation temperature due to local heat dissipation, and the white region gradually recovers to the colorless and transparent state.

Intelligent polymer gel is a new functional material having a sensitive response to external stimulations such as, typically, temperature, pH, solvent, concentration of salt, light, electric field, chemical substances, and etc. Temperature-sensitive polymer gel is an intelligent gel having a sensitive response to the stimulation of temperature.

Preferably, the temperature-sensitive polymer gel is an isopropylacrylamide (NIPA) polymer hydrogel, a poly N-vinyl caprolactam (PNVCL) hydrogel, or a β-hydroxypropyl acrylate-N-cinnamoyloxymethacrylamide (CMMAM) copolymer hydrogel, etc.

More preferably, isopropylacrylamide (NIPA) polymer hydrogel used for the intelligent tissue mimicking ultrasonic phantom comprises isopropylacrylamide, water; an initiating reductant, a crosslinking agent, an initiating oxidant; and a lower critical solution temperature conditioner that is a denaturation temperature regulator, wherein the weight percentage of each component is: isopropylacrylamide of 8-15%, denaturation temperature regulator of 0-4%, initiating reductant of 0.02-0.05%, crosslinking agent of 0.1-0.15%, initiating oxidant of 0.03-0.07%, and 91.85-80.73% of water, and the denaturation temperature is between 30° C. and 70° C. When the content of the denaturation temperature regulator is 0, the lower critical solution temperature (i.e., the denaturation temperature) of the intelligent tissue mimicking ultrasonic phantom of this invention is 30° C. The denaturation temperature varies from 30° C. to 70° C. by adjusting the amount of the regulator according to different needs.

In order to prevent microbiological contamination during storage and use, it is preferable that the isopropylacrylamide (NIPA) polymer hydrogel further comprises a preservative of 0-0.4% weight percentage. The preservative used is one selected from the group comprising Kathon (chemical name: mixture of 5-chloro-2-methyl-4-isothiazoline-3-one and 2-methyl-4-isothiazoline-3-one, molecular formula: $C_4H_4ClNOS+C_4H_5NOS$, molecular weight: 149.56+115.06, Cas No.: 55965-84-9), sodium benzoate (molecular formula: $C_7H_5NaO_2$, molecular weight: 144.1, Cas No.: 532-32-1), Nipagin ester/Methylparaben (chemical name: methyl p-hydroxybenzoate, molecular formula: $C_8H_8O_3$, molecular weight: 152.2, Cas No.: 99-76-3), phenoxyethanol (molecular formula: $C_8H_{10}O_2$, molecular weight: 138.16, Cas No.: 122-99-6). It is more preferable that the preservative used is phenoxyethanol in the present invention.

The above mentioned initiator is a substance containing weak bond, which produce an active centre for free radical polymerization. Under the action of the decomposition activation energy, covalent bond breaks to generate free radicals. In a general free radical polymerization system, the polymerization temperature is between 40° C. and 100° C. to provide sufficient activation energy. The initiators used in the present invention are an initiating reductant and an initiating oxidant, which is formed by adding a reductant to a peroxide initiator to generate free radicals by oxidation-reduction reactions. Such a system is called oxidation-reduction initiating system, or oxidation-reduction initiator. The decomposition activation energy can be reduced by using an oxidation-reduction initiator, so that the polymerization can be conducted at low temperatures (15-25° C.), which is beneficial in improving the quality of the polymer and reducing the requirements on the reaction environment for convenient operation.

The aforesaid crosslinking agent is a compound comprising a plurality of non-conjugated double bonds, which serves to convert the linear crosslinked structure of isopropylacrylamide formed by free radicals initiation to a three-dimensional network structure, so as to shape the gel.

Preferably, the water used is deionized and degassed water, the crosslinking agent is N,N'-methylene bisacrylamide, the initiating oxidant is ammonium persulfate, and the initiating reductant is sodium metabisulfite.

Preferably, the denaturation temperature regulator is acrylamide.

In the present invention, acrylamide is hydrophilic while isopropylacrylamide monomer is hydrophobic, therefore, the hydrophilicity of the entire system can be enhanced by adding acrylamide to the gel formed by polymerization of isopropylacrylamide, which increases the number of hydrogen bonds in the system. Since the thermal phase transition of a gel is caused by the breaking up of hydrogen bonds in the system, an increase in hydrogen bonds would increase the phase transition temperature of the system. Therefore, the denaturation temperature regulator is used to adjust the lower critical solution temperature (LCST) of the temperature-sensitive gel.

The applicant filed a patent application with the title "Method for Preparing Monomer of a Temperature-sensitive Poly(isopropylacrylamide)" at the Chinese Patent Office on Feb. 7, 2007, the application number being 200710003153.1. The isopropylacrylamide used in the present invention may be the monomer of poly(isopropylacrylamide) prepared according to this patent application "Method for Preparing Monomer of a Temperature-sensitive Poly(isopropylacrylamide)".

Test results shows that acoustic property and other physical characteristics of the intelligent tissue mimicking ultrasonic phantom according to the present invention are substantially the same as those of a biological tissue: acoustic velocity: 1500-1550 m/s; acoustic impedance: $(1.50\text{-}1.60)\times10^6$ Pa·s/m; density: 1.01-1.06 g/cm$^3$; and a denaturation temperature, i.e., a Lower Critical Solution Temperature (LCST) or a Volume Phase Transition Temperature at which the volume of the phantom changes, adjustable in the range of 30-70° C. by changing the ratio of the raw materials. When radiated with focused ultrasound, the tissue mimicking ultrasonic phantom, i.e. the isopropylacrylamide (NIPA) polymer hydrogel, in the focal region of the focused ultrasound changes from a colorless and transparent appearance to a opaque white appearance when the temperature of the focal region reaches the denaturation temperature due to an accumulation of ultrasonic energy, such that the morphology of the focal region of the focused ultrasound is clearly shown. When the focused ultrasonic radiation stops, the white region gradually reverts back to the colorless and transparent state as the temperature of the focal region becomes lower than the denaturation temperature due to local heat dissipation.

The mechanism of using the intelligent tissue mimicking ultrasonic phantom according to the present invention in showing the focal region of the focused ultrasound is as follows:

(1) As the intelligent tissue mimicking ultrasonic phantom is an intelligent polymer material, such has substantially the same acoustic property and other physical characteristics as those of a biological tissue. Acoustic velocity: 1500-1550 m/s; acoustic impedance: $(1.50\text{-}1.60)\times10^6$ Pa·s/m; density: 1.01-1.06 g/cm$^3$.

(2) At the focus of the focused ultrasound, the ultrasonic intelligent phantom is strongly stimulated by the overall effect of mechanical effects, thermal effects and cavity effects, particularly thermal effects, of the ultrasound. When the energy of the focused ultrasound reaches a certain intensity threshold causing that the temperature of the focus point reaches the denaturation temperature, the internal molecular structure of the ultrasonic intelligent phantom changes in its spatial arrangement (conformation), leading to a change in the appearance from colorless and transparent to white opaque (an emulsion). (Note: conformational change is phase transition which is also called phase separation.)

(3) With the deposition and diffusion of ultrasonic energy at the focal point, the area with change of the spatial conformation of phantom changes correspondingly, and the area with white (or opaque) appearance increases accordingly. This change is reversible within a certain range of ultrasonic intensity. With the disappearance of the ultrasound irradiation, the dissipation of heat, and the decrease in temperature, the changed spatial conformation restores the original state by self-absorption of water, that is, the white (or opaque) region reverts to the colorless and transparent state. That is why such a phantom is called an intelligent phantom.

(4) The denaturation temperature designed for this ultrasonic intelligent phantom is close to the coagulation necrosis temperature of a biological tissue, and the white (or opaque) region shown corresponds to the biological focal region induced by HIFU on the biological tissue. The denaturation temperature can also be adjusted by changing the ratio of the raw materials, so as to be applicable for different research purposes.

A method of making an isopropylacrylamide (NIPA) polymer hydrogel for an intelligent tissue mimicking ultrasonic phantom, including the following steps:

1. determining the formulation of the isopropylacrylamide (NIPA) polymer hydrogel, the weight percentage of each component being: 8-15% of isopropylacrylamide, 0-4% of denaturation temperature (LCST) regulator, 0.02-0.05% of initiating reductant, 0.1-0.15% of crosslinking agent, 0.03-0.07% of initiating oxidant, and 91.85-80.73% of water;

2. dissolving the isopropylacrylamide monomer in a portion of the water, and mass ratio of the monomer to water can be (0.1-0.2): 1;

3. adding a crosslinking agent to the solution obtained in step 2, and dissolving the same by stirring;

4. dissolving the initiating reductant and the initiating oxidant in a portion of the water, respectively, and the concentration can be 1-20%;

5. mixing the aqueous solutions of the isopropylacrylamide monomer, the crosslinking agent, and the initiating reductant uniformly in a container;

6. replacing the air at the surface of and around the container with nitrogen, which can be for 1 to 3 minutes;

7. adding the initiating oxidant aqueous solution to the container, mixing sufficiently and replacing the air at the surface of and around the liquid with nitrogen continuously;

8. sealing the container in a pure nitrogen environment after the addition of the initiating oxidant aqueous solution is completed. The solution in the container reacts for 3 to 24 hours, the temperature being controlled at 15° C.-25° C., so as to obtain a gel product;

9. washing the obtained gel product with water repeatedly at room temperature, wherein every washing comprises a cycle of soaking the surface with deionized and degassed water for several hours and drying for another several hours after discarding the water, and the cycle is repeated to remove toxicities of residual monomers and initiators on the surface which react incompletely.

In the whole process, the operation temperature is controlled in the range of 15° C.-25° C. If the temperature is too high, polymerization will occur during operation (explosive polymerization); if the temperature is too low, by contrast, it is difficult for polymerization to occur.

Preferably, in step 1, the denaturation temperature regulator of the isopropylacrylamide (NIPA) polymer gel composition is acrylamide with weight percentage of 0-4% in the polymer gel; in step 2, acrylamide can be added to the aqueous solution of the isopropylacrylamide monomer to change the LCST for fulfilling requirements of different uses. The change of the LCST can be achieved by adjusting the ratio of isopropylacrylamide to acrylamide. The LCST increases with the decrease of the molar ratio of isopropylacrylamide to acrylamide. When the molar ratio of isopropylacrylamide to acrylamide varies between (100~70):(0~30), the LCST can be adjusted in a range of 30° C.-70° C. Specifically, if acrylamide is not added, the LCST is maintained at 30° C., i.e., the LCST of poly(N-isopropylacrylamide) (PNIPA) hydrogel; if the molar ratio of isopropylacrylamide to acrylamide is 95:5, the LCST is 40° C.; if the molar ratio of isopropylacrylamide to acrylamide is 80:20, the LCST is 60° C.; and if the molar ratio of isopropylacrylamide to acrylamide is 70:30, the LCST is 70° C.

The water used is preferred to be double distilled deionized water. Deionized water is suitable for chemical reactions; however, water deionized by merely osmosis filtration through ion exchange column still cannot remove microorganisms in the water. Double distilled deionized water is advantageous in that, it is suitable for a chemical reaction, and it is free of microbial contamination. Therefore, changes resulted from microbial contamination in the gel is avoided. More preferably, the water used in the synthesis is degassed water.

Preferably, in step 1, the isopropylacrylamide polymer hydrogel further comprises a preservative with weight percentage of 0 to 0.4%; simultaneously, in step 3, the preservative added to the solution in step 2 is also included, and the preservative is dissolved in the solution in step 2 together with the crosslinking agent by stirring.

Preferably, in step 2, the mixture can be properly heated to assist in dissolving the isopropylacrylamide monomer, but the temperature should not exceed 40° C., and the solution upon heating should be cooled to below 25° C. before the subsequent operations.

Preferably, the elasticity of the gel can be adjusted by changing the amount of the crosslinking agent, that is, the elasticity of the gel can be changed by changing the amount of the crosslinking agent. It is preferable to use N,N'-methylene bisacrylamide as the crosslinking agent.

It is preferable to use ammonium persulfate as the initiating oxidant, and sodium metabisulfite as the initiating reductant.

Preferably, in step 8, the reaction in the sealed container is carried out under nitrogen atmosphere to exclude oxygen in the air from the polymerization reaction to ensure the smooth polymerization and the quality of the gel. The container containing the well-mixed raw materials is sealed in a commonly available plastic bag with good sealing performance, the air in the bag is then replaced by nitrogen, and the bag is then tied to maintain the pure nitrogen environment inside.

The container may be a glass beaker or other transparent containers. The nitrogen quality is of general industry standard, and the nitrogen may be supplied by a compressed gas cylinder.

Preferably, in step 9, the gel is washed for 5 cycles, each with double distilled deionized water soaking the surface for 12 hours, and then dried for another 12 hours after discarding the water. It is cumbersome if there are too many cycles; if there are too few cycles, the residual monomers on the surface cannot be effectively removed. For each cycle, there is an immersion in water step for 12 hours and a drying step for 12 hours. The desired effect cannot be achieved if the time is too short; if the time is too long, there will be a significant expansion in the volume of the gel.

Preferably, the method further includes the following step:

10. In step 9, after the gel is washed, a small amount of preservative solution prepared with distilled water is added to wet the surface of the gel, wherein the preservative can be Kathon, formaldehyde, or Nipagin series, and the concentration of the preservative solution prepared with distilled water is: 40-100 μg/mL for a Kathon solution, 0.5-1 mg/mL for a formaldehyde solution, and 5-10 mg/mL for a Nipagin solution.

More preferably, a small amount of Kathon solution prepared with distilled water is added to wet the surface of the gel for antisepsis purpose. Using formaldehyde in the antiseptic material will affect the transparency of the gel. Nipagin is not readily soluble in water, which affects the antisepsis effect.

The intelligent tissue mimicking ultrasonic phantom according to the present invention has the following advantages:

1. The ultrasonic intelligent phantom is highly transparent. When phase transition occurs at the denaturation temperature point upon radiation with focused ultrasound, the focal region formed therein has a clear morphology with well-defined boundary. That is, when the temperature is above the denaturation temperature, the opaque phase resulted can clearly show the morphology of the focal region of focused ultrasound.
2. With ultrasonic radiation ceases, the temperature is reduced, and the denatured region (appearance changed to white) can be reverted to be transparent (when the temperature is lower than the denaturation temperature, the time of phase transition depends on the volume, where the phase transition occurs most rapidly in 1 second), therefore, the phantom is intelligent, and can be used repeatedly.
3. The denaturation temperature of the phantom can be adjusted in the range of 30° C.-70° C. by changing the ratio of the raw materials or by adding an appropriate modifier. By contrast, protein phantoms only have a single and higher denaturation temperature, while the denaturation temperature of the ultrasonic intelligent phantom can be adjusted in the range of 30° C.-70° C. The ultrasonic intelligent phantom has more applications as such can be prepared to have a same denaturation temperature with that of simulation of biological tissues, which is based on the requirement of the tissue to be mimicked and different biological tissues have different coagulation necrosis temperatures.
4. With the unique formulation technology, the synthesis of the phantom can be carried out at room temperature, and the production of the phantom is simple.
5. The phantom is prepared using deionized and degassed water, which almost contains no air therein, which minimizes the effect of bubbles generated by cavity effects upon the focal region during ultrasonic radiation.
6. Not only the raw materials but also the preparation process of the ultrasonic intelligent phantom can be in strict uniformity. Besides, the phantom is a polymer and is free of bioactive substances such as proteins, resulting in good stability. A preservative can be added during the synthesis if necessary, which further ensures the stability of the phantom.
7. The quality of all the raw materials and the ratio according to the formulation can be consistent, and thereby ensuring the consistency of the properties of the ultrasonic intelligent phantom, and achieving standardization of the phantom.

DETAILED DESCRIPTION OF THE PREFERRED EMBODIMENTS

Specific but non-limiting working examples for preparing isopropylacrylamide (NIPA) polymer hydrogels as the intelligent tissue mimicking ultrasonic phantoms of the present invention are illustrated as follows.

EXAMPLE 1

An Intelligent Tissue Mimicking Ultrasonic Phantom having a Denaturation Temperature, i.e., LCST, of 30° C.

Ratio of raw materials:

| | |
|---|---|
| Isopropylacrylamide | 100.0 g |
| Initiating reductant, sodium metabisulfite | 0.5 g |
| Crosslinking agent, N,N'-methylene bisacrylamide | 1 g |
| Initiating oxidant, ammonium persulfate | 0.5 g |
| water (deionized and degassed water) | 898 g |

Steps:

1) dissolving the isopropylacrylamide monomer in a portion of the water, and mass ratio of the monomer to water is 0.15:1;

2) adding a crosslinking agent to the solution obtained in step 1), and dissolving the same by stirring;

3) dissolving the initiating reductant and the initiating oxidant in portions of the water, respectively, the concentrations of the two solutions thus obtained both being 10%;

4) mixing the aqueous solutions of the isopropylacrylamide monomer, the crosslinking agent, and the initiating reductant uniformly in a container;

5) packaging the container within a freshness protection plastic bag having good sealing performance, and replacing the air at the surface of and around the container with nitrogen for 4 minutes;

6) adding the aqueous solution of the initiating oxidant to the container, and mixing sufficiently while replacing the air in the bag with nitrogen for 3 minutes; then fastening the bag to maintain the internal pure nitrogen environment;

7) sealing the container for reacting for further 5 hours, the temperature being controlled at 20° C., so as to obtain a gel product;

8) washing the gel with water for five times, each wash comprising soaking the surface with deionized and degassed water for 12 hours and drying for another 12 hours after discarding the water; a small amount of Kathon solution (with a concentration of 60 μg/mL) prepared with distilled water can be added to wet the surface of the gel.

Test results of the prepared isopropylacrylamide (NIPA) polymer hydrogel, i.e., the intelligent tissue mimicking ultrasonic phantom, according to the present invention show a denaturation temperature, i.e., a Lower Critical Solution Temperature (LCST), of 30° C., and acoustic and physical characteristics: acoustic velocity: 1528 m/s; acoustic impedance: $1.56\times10^6$Pa·s/m; and density: 1.02 g/cm$^3$. When JC type focused ultrasound tumor therapy system (produced by Chongqing Haifu (HIFU) Technology Co., Ltd.) is used to focus ultrasound at the phantom, the spatial arrangement (conformation) of the internal molecular structure of the tissue mimicking ultrasonic phantom changes, i.e., phase transition, leading to a change in appearance from colorless and transparent to opaque white when the temperature of the focal region goes above the denaturation temperature of 30° C., due to an accumulation of ultrasonic energy. With the deposition and diffusion of ultrasonic energy at the focal point, the area in which a change of the spatial conformation of the phantom takes place expands, and the white area expands accordingly, and the focal region of the white area formed therein has a clear morphology with well-defined boundary. When the focused ultrasound radiation stops, with the disappearance of ultrasound irradiation, the temperature of the focal region of the focused ultrasound decreases correspondingly, and the changed spatial conformation reverts to the original state when the temperature turns below the denaturation temperature of 30° C., that is, the white region reverts to the colorless and transparent state. That is, at a certain range of ultrasonic intensity, the phase transition of the intelligent tissue mimicking ultrasonic phantom according to the present invention is reversible, and the white region can revert to the transparent state, therefore, the phantom is intelligent, and can be used repeatedly. Comparing with disposable protein phantom of the prior art, the phantom according to the present invention reduces costs of use, saves resources, and benefits the environment.

EXAMPLE 2

An Intelligent Tissue Mimicking Ultrasonic Phantom having a Denaturation Temperature, i.e., LCST, of 40° C.

Ratio of raw materials:

| | |
|---|---|
| Isopropylacrylamide | 100.0 g |
| Denaturation temperature regulator, acrylamide | 3.31 g |
| Initiating reductant, sodium metabisulfite | 0.34 g |
| Crosslinking agent, N,N'-methylene bisacrylamide | 1 g |
| Initiating oxidant, ammonium persulfate | 0.5 g |
| water (deionized and degassed water) | 895 g |

Steps:

1) dissolving the isopropylacrylamide monomer and acrylamide in a portion of the water, and mass ratio of the monomer to water is 0.15:1;

2) adding a crosslinking agent to the solution obtained in step 1), and dissolving the same by stirring;

3) dissolving the initiating reductant and the initiating oxidant in portions of the water, respectively, the concentrations of the two solutions thus obtained both being 1%;

4) mixing the aqueous solutions of the isopropylacrylamide monomer, the crosslinking agent, and the initiating reductant uniformly in a container;

5) packaging the container within a freshness protection plastic bag having good sealing performance, and replacing the air at the surface of and around the container with nitrogen for 5 minutes;

6) adding the aqueous solution of the initiating oxidant to the container, and mixing sufficiently while replacing the air in the bag with nitrogen for 3 minutes; then fastening the bag to maintain the internal pure nitrogen environment;

7) sealing the container for reacting for further 24 hours, the temperature being controlled at 15° C., so as to obtain a gel product;

8) washing the gel with water for five times, each wash comprising soaking the surface with deionized and degassed water for 12 hours and drying for another 12 hours after discarding the water; a small amount of Kathon solution (with a concentration of 80 μg/mL) prepared with distilled water can be added to wet the surface of the gel.

Test results of the prepared isopropylacrylamide (NIPA) polymer hydrogel, i.e., the intelligent tissue mimicking ultrasonic phantom, according to the present invention show a denaturation temperature, i.e., a Lower Critical Solution Temperature (LCST), of 40° C., and acoustic and other physical characteristics: acoustic velocity: 1522 m/s; acoustic impedance: $1.54\times10^6$Pa·s/m; and density: 1.01 g/cm$^3$. Other properties are the same as those of Example 1.

EXAMPLE 3

An Intelligent Tissue Mimicking Ultrasonic Phantom having a Denaturation Temperature, i.e., LCST, of 60° C.

Ratio of raw materials:

| | |
|---|---|
| Isopropylacrylamide | 100.0 g |
| Denaturation temperature regulator, acrylamide | 15.7 g |
| Initiating reductant, sodium metabisulfite | 0.4 g |
| Crosslinking agent, N,N'-methylene bisacrylamide | 1.2 g |
| Initiating oxidant, ammonium persulfate | 0.6 g |
| water (deionized and degassed water) | 882 g |

Steps:

1) dissolving the isopropylacrylamide monomer and acrylamide in a portion of the water, and mass ratio of the monomer to water is 0.18:1;

2) adding a crosslinking agent to the solution obtained in step 1), and dissolving the same by stirring;

3) dissolving the initiating reductant and the initiating oxidant in portions of the water, respectively, the concentrations of the two solutions thus obtained both being 20%;

4) mixing the aqueous solutions of the isopropylacrylamide monomer, the crosslinking agent, and the initiating reductant uniformly in a container;

5) packaging the container within a freshness protection plastic bag having good sealing performance, and replacing the air at the surface of and around the container with nitrogen for 3 minutes;

6) adding the aqueous solution of the initiating oxidant to the container, and mixing sufficiently while replacing the air in the bag with nitrogen for 1 minute; then fastening the bag to maintain the internal pure nitrogen environment;

7) sealing the container for reacting for further 10 hours, the temperature being controlled at 18° C., so as to obtain a gel product;

8) washing the gel with water for five times, each wash comprising soaking the surface with double distilled deionized water for 12 hours and drying for another 12 hours after discarding the water; a small amount of Kathon solution (with a concentration of 50 μg/mL) prepared with distilled water can be added to wet the surface of the gel.

Test results of the prepared isopropylacrylamide (NIPA) polymer hydrogel, i.e., the intelligent tissue mimicking ultrasonic phantom, according to the present invention show a denaturation temperature, i.e., a Lower Critical Solution Temperature (LCST), of 60° C., and acoustic and other physical characteristics: acoustic velocity: 1530 m/s; acoustic impedance: $1.55\times10^6$ Pa·s/m; and density: 1.01 g/cm$^3$. Other properties are the same as those of Example 1.

EXAMPLE 4

An Intelligent Tissue Mimicking Ultrasonic Phantom having a Denaturation Temperature, i.e., LCST, of 70° C.

Ratio of raw materials:

| | |
|---|---|
| Isopropylacrylamide | 100.0 g |
| Denaturation temperature regulator, acrylamide | 27 g |
| Initiating reductant, sodium metabisulfite | 0.4 g |
| Crosslinking agent, N,N'-methylene bisacrylamide | 1.2 g |
| Initiating oxidant, ammonium persulfate | 0.5 g |
| water (deionized and degassed water) | 871 g |

Steps:

1) dissolving the isopropylacrylamide monomer and acrylamide in a portion of the water, and mass ratio of the monomer to water is 0.15:1;

2) adding a crosslinking agent to the solution obtained in step 1), and dissolving the same by stirring;

3) dissolving the initiating reductant and the initiating oxidant in portions of the water, respectively, the concentrations of the two solutions thus obtained both being 15%;

4) mixing the aqueous solutions of the isopropylacrylamide monomer, the crosslinking agent, and the initiating reductant uniformly in a container;

5) packaging the container within a freshness protection plastic bag having good sealing performance, and replacing the air at the surface of and around the container with nitrogen for 5 minutes;

6) adding the aqueous solution of the initiating oxidant to the container, and mixing sufficiently while replacing the air in the bag with nitrogen for 3 minutes; then fastening the bag to maintain the internal pure nitrogen environment;

7) sealing the container for reacting for further 20 hours, the temperature being controlled at 25° C., so as to obtain a gel product;

8) washing the gel with water for five times, each wash comprising soaking the surface with double distilled deionized water for 12 hours and drying for another 12 hours after discarding the water; a small amount of Kathon solution (with a concentration of 40-100 μg/mL) prepared with distilled water can be added to wet the surface of the gel.

Test results of the prepared isopropylacrylamide (NIPA) polymer hydrogel, i.e., the intelligent tissue mimicking ultrasonic phantom, according to the present invention show a denaturation temperature, i.e., a Lower Critical Solution Temperature (LCST), of 70° C., and acoustic and other physical characteristics: acoustic velocity: 1549 m/s; acoustic impedance: $1.56\times10^{6}$Pa·s/m; and density: 1.01 g/cm$^3$. Other properties are the same as those of Example 1.

EXAMPLE 5

An Intelligent Tissue Mimicking Ultrasonic Phantom having a Denaturation Temperature, i.e., LCST, of 57° C.

Ratio of raw materials:

| | |
|---|---|
| Isopropylacrylamide | 85.0 g |
| Denaturation temperature regulator, acrylamide | 9.5 g |
| Initiating reductant, sodium metabisulfite | 0.2 g |
| Crosslinking agent, N,N'-methylene bisacrylamide | 1 g |
| Initiating oxidant, ammonium persulfate | 0.3 g |
| water (deionized and degassed water) | 898 g |

Steps:

1) dissolving the isopropylacrylamide monomer and acrylamide in a portion of the water, and mass ratio of the monomer to water is 0.15:1;

2) adding a crosslinking agent to the solution obtained in step 1), and dissolving the same by stirring;

3) dissolving the initiating reductant and the initiating oxidant in portions of the water, respectively, the concentrations of the two solutions thus obtained both being 10%;

4) mixing the aqueous solutions of the isopropylacrylamide monomer, the crosslinking agent, and the initiating reductant uniformly in a container;

5) packaging the container within a freshness protection plastic bag having good sealing performance, and replacing the air at the surface of and around the container with nitrogen for 3-5 minutes;

6) adding the aqueous solution of the initiating oxidant to the container, and mixing sufficiently while replacing the air in the bag with nitrogen for 2 minutes; then fastening the bag to maintain the internal pure nitrogen environment;

7) sealing the container for reacting for further 15 hours, the temperature being controlled at 18° C., so as to obtain a gel product;

8) washing the gel with water for five times, each wash comprising soaking the surface with double distilled deionized water for 12 hours and drying for another 12 hours after discarding the water; a small amount of Kathon solution (with a concentration of 90 μg/mL) prepared with distilled water can be added to wet the surface of the gel.

Test results of the prepared isopropylacrylamide (NIPA) polymer hydrogel, i.e., the intelligent tissue mimicking ultrasonic phantom, according to the present invention show a denaturation temperature, i.e., a Lower Critical Solution Temperature (LCST), of 57° C., and acoustic and other physical characteristics: acoustic velocity: 1541 m/s; acoustic impedance: $1.57\times10^{6}$ Pa·s/m; and density: 1.02 g/cm$^3$. And other properties are the same as those of Example 1.

EXAMPLE 6

An Intelligent Tissue Mimicking Ultrasonic Phantom having a Denaturation Temperature, i.e., LCST, of 52° C.

Ratio of raw materials:

| | |
|---|---|
| Isopropylacrylamide | 140.0 g |
| Denaturation temperature regulator, acrylamide | 10 g |
| Initiating reductant, sodium metabisulfite | 0.5 g |
| Crosslinking agent, N,N'-methylene bisacrylamide | 1.5 g |
| Initiating oxidant, ammonium persulfate | 0.7 g |
| Preservative, phenoxyethanol | 2 ml |
| water (deionized and degassed water) | 846 g |

Steps:

1) dissolving the isopropylacrylamide monomer and acrylamide in a portion of the water, and mass ratio of the monomer to water is 0.15:1;

2) adding a crosslinking agent and the preservative to the solution obtained in step 1), and dissolving the same by stirring;

3) dissolving the initiating reductant and the initiating oxidant in portions of the water, respectively, the concentrations of the two solutions thus obtained both being 15%;

4) mixing the aqueous solutions of the isopropylacrylamide monomer, the crosslinking agent, and the initiating reductant uniformly in a container;

5) packaging the container within a freshness protection plastic bag having good sealing performance, and replacing the air at the surface of and around the container with nitrogen for 5 minutes;

6) adding the aqueous solution of the initiating oxidant to the container, and mixing sufficiently while replacing the air in the bag with nitrogen for 3 minutes; then fastening the bag to maintain the internal pure nitrogen environment;

7) sealing the container for reacting for further 15 hours, the temperature being controlled at 25° C., so as to obtain a gel product;

8) washing the gel with water for five times, each wash comprising soaking the surface with double distilled deionized water for 12 hours and drying for another 12 hours after discarding the water; a small amount of Kathon solution (with a concentration of 40-100 μg/mL) prepared with distilled water can be added to wet the surface of the gel.

Test results of the prepared isopropylacrylamide (NIPA) polymer hydrogel, i.e., the intelligent tissue mimicking ultrasonic phantom, according to the present invention show a denaturation temperature, i.e., a Lower Critical Solution Temperature (LCST), of 52° C., and acoustic and other physical characteristics: acoustic velocity: 1536 m/s; acoustic impedance: $1.58\times10^6$ Pa·s/m; and density: 1.03 g/cm$^3$. Other properties are the same as those of Example 1.

The invention claimed is:

1. Method of using an intelligent tissue mimicking ultrasonic phantom in showing a focal region of a focused ultrasound comprising:

(a) providing a transparent intelligent tissue mimicking ultrasonic phantom, characterized in that said phantom is a temperature-sensitive polymer gel having the following acoustic properties and other physical characteristics: acoustic velocity: 1500-1550 m/s; acoustic impedance: (1.50-1.60)* $10^6$ Pa·s/m; density: 1.01-1.06 g/cm$^3$"; and a denaturation temperature, namely, a Lower Critical Solution Temperature (LCST) or a Volume Phase Transition Temperature at which the volume of the phantom changes, adjustable by changing ratios of raw materials, around which there is a reversible phase transformation between an opaque phase and a transparent phase;

(b) focusing ultrasound irradiation in the transparent intelligent tissue mimicking ultrasonic phantom at a focal point, whereby the ultrasonic phantom is stimulated by the overall effect of mechanical effects, thermal effects and cavity effects of the ultrasound, and the energy of the focused ultrasound reaches an intensity threshold causing the temperature at the focal point to reach the denaturation temperature, at which the internal molecular structure of the ultrasonic phantom changes from an original spatial arrangement conformation having a colorless and transparent appearance to a changed spatial conformation having a white or opaque appearance; whereby with continued deposition and diffusion of ultrasonic energy at the focal point, a focal region with white or opaque appearance increases accordingly such that a focal region of the focused ultrasound is clearly shown in the ultrasonic phantom; and (c) stopping the ultrasound irradiation, whereby with a dissipation of heat, and a corresponding decrease in temperature to below the denaturation temperature, the focal region with white or opaque appearance in the ultrasonic phantom reverts to the colorless and transparent appearance.

2. The method according to claim 1, characterized in that said temperature-sensitive polymer gel is a isopropylacrylamide polymer hydrogel, a poly N-vinyl caprolactam hydrogel, or a β-hydroxypropyl acrylate -N-cinnamoyloxymethacrylamide copolymer hydrogel.

3. The method according to claim 2, characterized in that said temperature-sensitive polymer gel is an isopropylacrylamide polymer hydrogel, and wherein said isopropylacrylamide polymer hydrogel used for the intelligent tissue mimicking ultrasonic phantom is made from a formulation comprising isopropylacrylamide, water; an initiating reductant, a crosslinking agent, an initiating oxidant; and a denaturation temperature regulator, wherein the weight percentage of each component is: 8-15% of isopropylacrylamide monomer, 0-4% of the denaturation temperature regulator, 0.02-0.05% of the initiating reductant, 0.1-0.15% of the crosslinking agent, 0.03-0.07% of the initiating oxidant, and 91.85-80.73% of water, and the denaturation temperature is between 30° C. and 70° C.

4. The method according to claim 3, characterized in that said water is deionized and degassed water, said crosslinking agent is N, N'-methylene bisacrylamide (BIS), said initiating oxidant is ammonium persulfate (APS), and said initiating reductant is sodium metabisulfite.

5. The method according to claim 3, characterized in that said denaturation temperature regulator is acrylamide.

6. The method according to claim 1, wherein the intelligent tissue mimicking ultrasonic phantom provided in step (a) comprises an isopropylacrylamide polymer hydrogel which is made by a method including steps of:

(1) determining a formulation of a isopropylacrylamide (NIPA) polymer hydrogel, weight percentage of each component being: 8-15% of isopropylacrylamide, 0-4% of denaturation temperature (LCST) regulator, 0.02-0.05% of initiating reductant, 0.1-0.15% of crosslinking agent, 0.03-0.07% of initiating oxidant, and 91.85-80.73% of water;

(2) dissolving an isopropylacrylamide monomer in a portion of the water;

(3) adding a crosslinking agent to the solution obtained in step 2, and dissolving the same by stirring;

(4) dissolving the initiating reductant and the initiating oxidant in portions of the water, respectively;

(5) mixing aqueous solutions of the isopropylacrylamide monomer, the crosslinking agent, and the initiating reductant uniformly in a container;

(6) replacing the air at the surface of and around the container with nitrogen;

(7) adding the aqueous solution of the initiating oxidant to the container, and mixing sufficiently while replacing the air at the surface of and around the liquid with nitrogen continuously;

(8) sealing the container in a pure nitrogen environment after adding the aqueous solution of the initiating oxidant is completed, allowing the solution to react for 3 to 24 hours, the temperature being controlled at 15° C.-25° C., so as to obtain a gel product.

7. The method according to claim 6, wherein the method of making the isopropylacrylamide polymer hydrogel further comprises washing the obtained gel product with water for a plurality of times at room temperature, wherein every washing comprises a cycle of soaking its surface with deionized and degassed water for several hours and drying for another several hours after discarding the water, the cycle is repeated for a plurality of times to remove residual monomers and initiators on the surface, so as to eliminate toxicity.

8. The method according to claim 6, characterized in that, in step (1) of making the isopropylacrylamide polymer hydrogel, a denaturation temperature regulator is acrylamide; and in step (2), acrylamide is added to the aqueous solution of the isopropylacrylamide monomer.

9. The method according to claim 8, characterized in that, when molar ratio of isopropylacrylamide to acrylamide varies between (100~70): (0~30), denaturation temperature can be adjusted in a range of 30° C.-70° C.

10. The method according to claim 6, characterized in that, in step (2) of making the isopropylacrylamide polymer hydrogel, the mixture can be properly heated to help the dissolution of the isopropylacrylamide monomer, but the temperature does not exceed 40° C., and the solution upon heating is cooled to below 25° C. before subsequent operations.

11. The method according to claim 6, characterized in that, in step (1) of making the isopropylacrylamide polymer hydrogel, the water used is deionized and degassed water.

12. The method according to claim 6, characterized in that, an elasticity of the gel can be changed by adjusting the content of the crosslinking agent according to usage requirements, and N, N'-methylene bisacrylamide is used as the crosslinking agent.

13. The method according to claim 6, characterized in that, said initiating oxidant is ammonium persulfate, and said initiating reductant is sodium metabisulfite.

14. The method according to claim 6, characterized in that, in step (8) of making the isopropylacrylamide polymer hydrogel, the reaction in the sealed container is carried out under nitrogen atmosphere to exclude the oxygen in the air from the polymerization reaction to ensure smooth polymerization and quality of the gel.

15. The method according to claim 8, further characterized in that said water is deionized and degassed water, said crosslinking agent is N, N'-methylene bisacrylamide (BIS), said initiating oxidant is ammonium persulfate (APS), and said initiating reductant is sodium metabisulfite.

16. The method according to claim 8, characterized in that, when molar ratio of isopropylacrylamide to acrylamide varies between (95~70): (5~30), denaturation temperature can be adjusted in a range of 40° C.-70° C.

17. The method according to claim 1, wherein the temperature-sensitive polymer gel is an isopropylacrylamide polymer hydrogel, said isopropylacrylamide polymer hydrogel used for the intelligent tissue mimicking ultrasonic phantom is made from a formulation comprising isopropylacrylamide, water, an initiating reductant, a crosslinking agent, an initiating oxidant, and a denaturation temperature regulator, wherein the weight percentage of each component is: 8.6-13.9% of isopropylacrylamide monomer, 0-2.74% of the denaturation temperature regulator, 0.02-0.05% of the initiating reductant, 0.1-0.15% of the crosslinking agent, 0.03-0.07% of the initiating oxidant, and 84.74-90.34% of water, and the denaturation temperature is between 30° C. and 70° C.

18. The method according to claim 1, wherein the temperature-sensitive polymer gel is an isopropylacrylamide polymer hydrogel, said isopropylacrylamide polymer hydrogel used for the intelligent tissue mimicking ultrasonic phantom is made from a formulation comprising isopropylacrylamide, water; an initiating reductant, a crosslinking agent, an initiating oxidant; and acrylamide as a denaturation temperature regulator, wherein the weight percentage of each component is: 8.6-13.9% of isopropylacrylamide monomer, 0.33-2.7% of the acrylamide as a denaturation temperature regulator, 0.02-0.05% of the initiating reductant, 0.1-0.15% of the crosslinking agent, 0.03-0.07% of the initiating oxidant, and 84.74-90.34% of water, and the denaturation temperature is between 40° C. and 70° C.

19. The method of claim 3, wherein said initiating oxidant is ammonium persulfate, and said initiating reductant is sodium metabisulfite.

20. The method according to claim 1, further comprising repeatedly using the ultrasonic phantom provided in step (a) after the focal region with white or opaque appearance reverts to the colorless and transparent appearance in step (c), by repeating steps (b) and (c).

* * * * *